United States Patent [19]
Knapp, Jr.

[11] Patent Number: 5,453,508
[45] Date of Patent: Sep. 26, 1995

[54] MANUFACTURE OF 4-ARYL-2-PERFLUOROALKYL-3-OXAZOLIN-5-ONE FROM ARYLGLYCINE

[75] Inventor: Paul W. Knapp, Jr., Bordentown, N.J.

[73] Assignee: American Cyanamid Company, Wayne, N.J.

[21] Appl. No.: 321,276

[22] Filed: Oct. 11, 1994

[51] Int. Cl.⁶ .................................................. C07D 263/42
[52] U.S. Cl. ............................................................ 548/228
[58] Field of Search ............................................... 548/228

[56] References Cited

U.S. PATENT DOCUMENTS

| | | | |
|---|---|---|---|
| 5,010,098 | 4/1991 | Brown et al. | 514/426 |
| 5,030,735 | 7/1991 | Addor et al. | 548/531 |
| 5,288,901 | 2/1994 | Doehner, Jr. et al. | 562/449 |

OTHER PUBLICATIONS

Wiley, R. H. Journal of Organic Chemistry, 12, 43–46 (1947).
Benages, I. A. and Albonico, S. M., Journal of Organic Chemistry, 43, 4273–4276 (1978).
Bartlett, P. A. and Barstow, J. F., Journal of Organic Chemistry, 1982, 47, 3933–3941.
Padwa, A.; Akiba, M.; Cohen, L. A. and MacDonald, J. G., Journal of Organic Chemistry, 1983, 48, 695–703.
Carter, H. E. and Hinman, J. W., The Hournal of Biological Chemistry, 178, 403–421 (1949).

*Primary Examiner*—Robert Gerstl
*Assistant Examiner*—Laura R. Cross
*Attorney, Agent, or Firm*—John W. Hogan, Jr.

[57] ABSTRACT

There is provided an efficient single step process to produce 4-aryl-2-perfluoroalkyl-3-oxazolin-5-one from arylglycine and a perfluoroacylating agent in the presence of a phosphorous trihalide and a solvent.

The oxazolinone is a key intermediate in the production of insecticidal, nematicidal and acaricidal arylpyrrole compounds.

15 Claims, No Drawings

MANUFACTURE OF 4-ARYL-2-PERFLUOROALKYL-3-OXAZOLIN-5-ONE FROM ARYLGLYCINE

BACKGROUND OF THE INVENTION

Arylpyrrole carbonitrile compounds and derivatives thereof are highly effective insecticidal, acaricidal and nematicidal agents. In particular 2-aryl-5-trifluoromethylpyrrole-3-carbonitrile compounds and their derivatives have been found to have a broad spectrum of activity at very low rates of application with effectiveness against resistant species. Methods to prepare said pyrrole compounds on a manufacturing scale include the 1,3-dipolar cycloaddition of the appropriate 3-oxazolin-5-one with 2-chloroacrylonitrile described in U.S. Pat. No. 5,030,735.

Methods known in the art to prepare 3-oxazolin-5-one compounds from glycine starting materials require either a 2 step synthesis which includes at least one equivalent of base for the first step amide formation and at least a second equivalent of base and/or an excess of dehydrating reagent such as an anhydride for the second step ring closure or an excess of an anhydride which acts as both an acylating agent and dehydrating agent to give the ring closed product in a single step. Both of these approaches require at least one equivalent of an acid scavenger for the initial amide formation and further may call for excesses of reagents which are known to be corrosive and hazardous.

It is an object of this invention to provide an effective single step procedure to prepare 4-aryl-2-perfluoroalkyl-3-oxazolin-5-one from aryl glycine which avoids the use of an additional acid scavenger (i.e., a second equivalent of base) and further eliminates the need for excessive amounts of potentially hazardous and corrosive acylating reagent.

It is a further object of this invention to provide an efficient and convenient source of a key intermediate in the production of arylpyrrole carbonitrile pesticidal agents.

SUMMARY OF THE INVENTION

There is provided a process for the manufacture of a 4-aryl-2-perfluoroalkyl-3-oxazolin-5-one compound of formula I

wherein n is an integer of 1, 2, 3, 4, 5, 6, 7 or 8;

A is

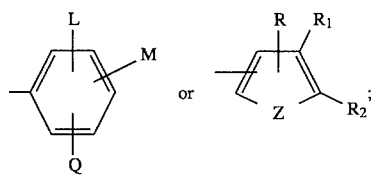

L is hydrogen or halogen;

M and Q are each independently hydrogen, halogen, CN, $NO_2$, $C_1$–$C_4$alkyl, $C_1$–$C_4$haloalkyl, $C_1$–$C_4$alkoxy, $C_1$–$C_4$haloalkoxy, $C_1$–$C_4$alkylthio, $C_1$–$C_4$alkylsulfinyl or when M and Q are on adjacent positions they may be taken together with the carbon atoms to which they are attached to form a ring in which MQ represents the structure —$OCH_2O$—, —$OCF_2O$— or —CH=CH—CH=CH—;

R, $R_1$ and $R_2$ are each independently hydrogen, halogen, $NO_2$, CHO or $R_1$ and $R_2$ may be taken together with the atoms to which they are attached to form a ring in which $R_1R_2$ is represented by the structure

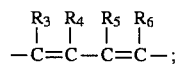

$R_3$, $R_4$, $R_5$ and $R_6$ are each independently hydrogen, halogen, CN or $NO_2$; and Z is O or S which comprises reacting an arylglycine of formula II

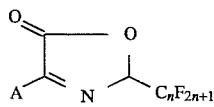 (II)

wherein A is described above with at least one molar equivalent of a compound of formula III, $C_nF_{2n+1}COX$ wherein n is described above and X is OH or Cl in the presence of about 0.4–1.1 molar equivalents of a phosphorous trihalide and a solvent or solvent mixture at a temperature of about 25°–100° C., and when X is OH, in the presence of at least one molar equivalent of a tri($C_1$–$C_4$alkyl)amine.

The formula I oxazolin-5-one is a key intermediate in the manufacture of a new class of highly effective arylpyrrole carbonitrile insecticides, acaricides and nematicides.

DETAILED DESCRIPTION OF THE INVENTION

Processes, to be useful on a manufacturing scale, preferentially produce key intermediate compounds in high to quantitative yield from simple and readily available starting materials in a minimum of reaction steps with reduced waste and recycle requirements.

It has now been found that 4-aryl-2-perfluoroalkyl-3-oxazolin-5-one compounds of formula I can be prepared on a manufacturing scale in a single step, in high to quantitative yield, directly from arylglycine and perfluoroacyl chloride or perfluorocarboxylic acid in the presence of about 0.4–1.1 molar equivalents, preferably about 0.4–0.6 molar equivalents of a phosphorous trihalide such as phosphorous trichloride or phosphorous tribromide and a solvent. Surprisingly, the presence of about 0.4–1.1 molar equivalents of a phosphorous trihalide allows the reaction to proceed in a single step without the need for excess acylating reagent or an additional equivalent of a base. Advantageously, no unwanted $\Delta^2$ isomer is formed, instead the desired $\Delta^3$ isomer product is obtained exclusively. The reaction is shown in Flow Diagram I wherein the phosphorous trihalide is $PCl_3$ and A, n and X are described hereinabove.

FLOW DIAGRAM I

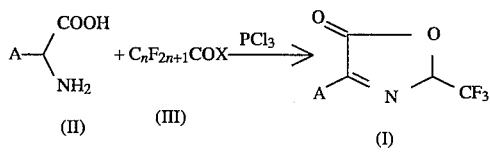

The formula I oxazolinone compound is a key intermediate in the manufacture of pesticidal arylpyrrole-3-carbonitrile compounds. The $\Delta^3$ isomer gives the desired regiochemistry in said pyrrole products. The use of the inventive process is shown in Flow Diagram II.

FLOW DIAGRAM II

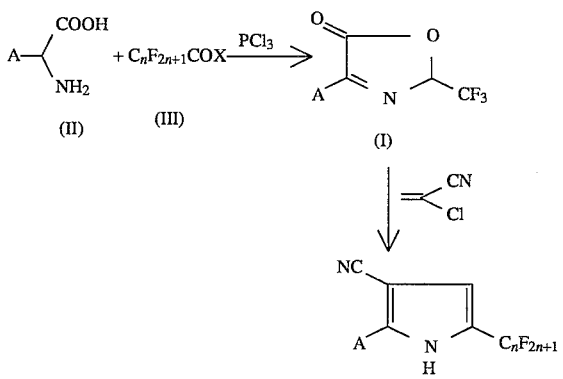

Arylglycines of formula II are described in U.S. Pat. No. 5,288,901 and the use of oxazolinone compounds of formula I in arylpyrrole preparation is described in U.S. Pat. No. 5,030,735.

Solvents useful in the inventive process may be any of the commonly known inert organic solvents such as aromatic hydrocarbons, e.g., halobenzene, toluene, xylene; nitriles, e.g., acetonitrile; carboxylic acid amides, e.g., dimethyl formamide, N-methylpyrrolidone; halogenated hydrocarbons, e.g., methylene chloride, ethylene dichloride, carbon tetrachloride and the like. These solvents may be used alone or in combination of two or more. Preferable solvents are aromatic hydrocarbons and nitriles alone or in combination with one another and with dimethyl formamide.

Reaction rate increases with increasing temperature, however exceedingly high temperatures will lead to decomposition and side-product formation, decreasing product yield and purity. Reaction temperatures of about 25° C. –110° C., preferably about 40° C. –65° C. are suitable. It is an advantage of this invention that processing parameters such as stirring and heat transfer are greatly improved.

When the acylating agent is a perfluorocarboxylic acid, a suitable organic amine base may be a tri($C_1$–$C_4$-alkyl)amine such as triethylamine.

In accordance with the process of the invention a formula II arylglycine in a suitable solvent, or solvent mixture, is sequentially treated with about 0.4–1.1, preferably 0.4–0.6, molar equivalents of a phosphorous trihalide, preferably phosphorous trichloride and a perfluoroacylating agent, preferably perfluoroacylchloride at a temperature range of about 40° –65° C. When the reaction is complete the product may be isolated using conventional procedures such as extraction, filtration and the like or, preferably, the reaction product solution may be used as is in the next manufacturing step in the pesticidal arylpyrrole production as shown in Flow Diagram II hereinabove.

Preferred Formula II compounds are those in which A is

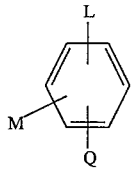

and M and Q are independently hydrogen, halogen, CN, $NO_2$, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, or $C_1$–$C_4$ alkylsulfinyl, with hydrogen, halogen and $C_1$–$C_4$ haloalkyl being especially preferred.

In order to provide a more clear understanding of the invention, the following examples are set forth below. These examples are merely illustrative and are not to be understood to limit the scope or underlying principals of the invention in any way.

The term HPLC designates high performance liquid chromatography. All parts are parts by weight unless otherwise designated.

EXAMPLE 1

Preparation of 4-(p-Chlorophenyl) -2-trifluoromethyl-3-oxazolin-5-one.

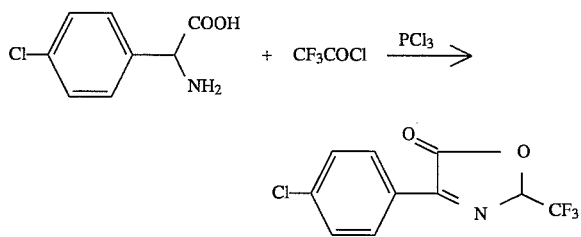

A solution of p-chlorophenylglycine (46.9 g, 0.25 mole) in a mixture of acetonitrile, xylenes and dimethyl formamide (74.8 w/w%, 24.9 w/w% and 0.3 w/w%, respectively) is treated sequentially with $PCl_3$ (21.3 g, 0.155 mole) and trifluoroacetyl chloride (34.8 g, 0.26 mole), held at 40° C. for 0.5 hour, heated at 60° –65° C. for 8 hours and allowed to cool to room temperature. The title product is obtained in quantitative yield by HPLC analysis.

EXAMPLE 2

Preparation of 4-Aryl- 2-perfluoroalkyl-3-oxazolin-5-one.

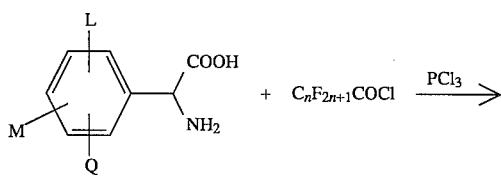

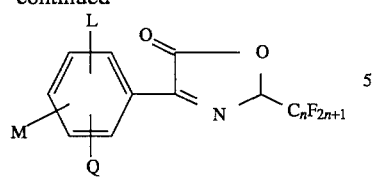

Using essentially the same procedure described in Example 1 and substituting the appropriate phenylglycine and perfluoroacyl chloride the following oxazolinones are prepared and shown in Table I.

TABLE I

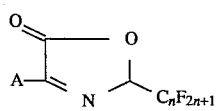

| L | M | Q | n | mp °C. |
|---|---|---|---|---|
| H | H | H | 1 | — |
| H | 4-Br | H | 1 | 48–51 |
| 3-Cl | H | 5-Cl | 1 | — |
| H | 4-Cl | H | 2 | 39–42 |
| H | 3-Cl | 4-Cl | 1 | yellow oil |
| H | 4-CF$_3$ | H | 1 | 39.0–40.5 |
| H | 3-Cl | 5-Cl | 2 | — |
| H | 4-Cl | H | 3 | 37.0–39.0 |
| 3-F | H | 5-F | 1 | — |
| H | 3-Cl | H | 1 | 63–65 |

EXAMPLE 3

Preparation of 4-(p-Chlorophenyl)-2-trifluoromethyl-3-oxazolin-5-one.

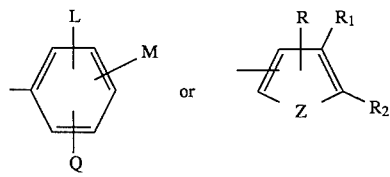

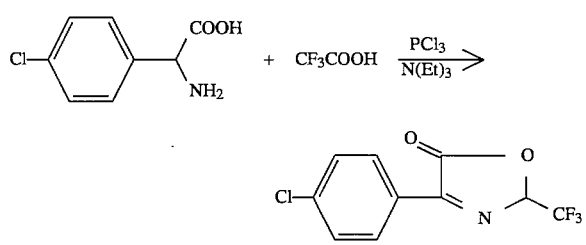

A mixture of p-chlorophenylglycine (49.9 g, 0.25 mole) in acetonitrile is treated with trifluoroacetic acid (42.7 g, 0.375 mole). This reaction mixture is treated dropwise with, sequentially, triethylamine (25.3 g, 0.25 mole) over a 0.25 hour period and PCl$_3$ (37.7 g, 0.275 mole) over a 0.25 hour period, heated at 65° C. for four hours and cooled to room temperature. The product is obtained in 97.4% yield by HPLC analysis.

I claim:
1. A process for the preparation of a compound of formula I

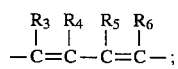

wherein
n is an integer of 1, 2, 3, 4, 5, 6, 7 or 8; and
A is

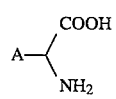

L is hydrogen or halogen;
M and Q are each independently hydrogen, halogen, CN, NO$_2$, C$_1$–C$_4$alkyl, C$_1$–C$_4$haloalkyl, C$_1$–C$_4$alkoxy, C$_1$–C$_4$haloalkoxy, C$_1$–C$_4$alkylthio, C$_1$–C$_4$alkylsulfinyl or when M and Q are on adjacent positions they may be taken together with the carbon atoms to which they are attached to form a ring in which MQ represents the structure —OCH$_2$O—, —OCF$_2$O— or —CH=CH—CH=CH—;
R, R$_1$ and R$_2$ are each independently hydrogen, halogen, NO$_2$, CHO or R$_1$ and R$_2$ may be taken together with the atoms to which they are attached to form a ring in which R$_1$R$_2$ is represented by the structure

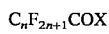

R$_3$, R$_4$, R$_5$ and R$_6$ are each independently hydrogen, halogen, CN or NO$_2$ and
Z is O or S
which comprises reacting a compound of formula II $$A-\underset{NH_2}{\underset{|}{CH}}-COOH \qquad (II)$$

with at least one molar equivalent of a compound of formula III $$C_nF_{2n+1}COX \qquad (III)$$

wherein n is described above and X is OH or Cl in the presence of about 0.4–1.1 molar equivalents of a phosphorous trihalide and a solvent or solvent mixture at a temperature of about 25°–110° C., and when X is OH, in the presence of at least one molar equivalent of a tri(C$_1$–C$_4$alkyl)amine.
2. The process according to claim 1 wherein the phosphorous trihalide is phosphorous trichloride.
3. The process according to claim 1 wherein the tri(C$_1$–C$_4$alkyl)amine is triethylamine.
4. The process according to claim 1 wherein X is Cl.
5. The process according to claim 1 wherein n is an integer of 1 or 2.

6. The process according to claim 1 wherein the solvent or solvent mixture is acetonitrile, dimethyl formamide, toluene, xylene or a combination thereof.

7. The process according to claim 1 wherein the temperature is about 40°–65° C.

8. The process according to claim 1 wherein A is

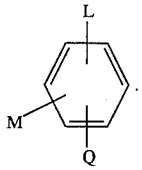

9. The process of claim 8 wherein M and Q are independently hydrogen, halogen, CN, $NO_2$, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, or $C_1$–$C_4$ alkylsulfinyl.

10. The process according to claim 9 wherein L is hydrogen and M and Q are independently hydrogen, halogen or $C_1$–$C_4$ haloalkyl.

11. The process according to claim 9 wherein the formula III compound is trifluoroacetyl chloride and the reaction temperature is about 40°–65° C.

12. The process according to claim 11 wherein the phosphorous trihalide is phosphorous trichloride and is present in the amount of about 0.4–0.6 molar equivalents.

13. The process according to claim 12 wherein the solvent or solvent mixture is acetonitrile, dimethyl formamide, toluene, xylene, or a combination thereof.

14. The process according to claim 13 wherein the formula II compound is a halophenylglycine.

15. The process according to claim 14 wherein the formula II compound is p-chlorophenylglycine.

* * * * *